US008545525B2

(12) United States Patent
Surti et al.

(10) Patent No.: US 8,545,525 B2
(45) Date of Patent: Oct. 1, 2013

(54) PLANAR CLAMPS FOR ANASTOMOSIS

(75) Inventors: Vihar Surti, Winston-Salem, NC (US); Tyler McLawhorn, Winston-Salem, NC (US); Richard W. Ducharme, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 231 days.

(21) Appl. No.: 12/909,218

(22) Filed: Oct. 21, 2010

(65) Prior Publication Data

US 2011/0106109 A1    May 5, 2011

Related U.S. Application Data

(60) Provisional application No. 61/257,654, filed on Nov. 3, 2009.

(51) Int. Cl.
*A61B 17/08* (2006.01)

(52) U.S. Cl.
USPC .............................. 606/153; 24/547

(58) Field of Classification Search
USPC ............... 606/139, 142, 144, 148, 151, 153, 606/155, 157, 158, 213; 24/67.3, 67.9, 455, 24/456, 485, 487–489, 493, 495, 499, 530, 24/531, 545–547; D19/65, 75; D8/395
See application file for complete search history.

(56) References Cited

U.S. PATENT DOCUMENTS

| | | | |
|---|---|---|---|
| 1,783,484 A * | 12/1930 | Ross | 24/547 |
| 3,057,028 A * | 10/1962 | Lorber | 24/67.9 |
| 3,299,883 A | 1/1967 | Rubens | |
| 3,358,676 A | 12/1967 | Frei et al. | |
| 3,674,014 A | 7/1972 | Tillander | |
| 3,709,214 A | 1/1973 | Robertson | |
| 4,022,208 A | 5/1977 | Valtchev | |
| 4,214,587 A | 7/1980 | Sakura, Jr. | |
| 4,899,744 A | 2/1990 | Fujitsuka et al. | |
| 5,081,997 A | 1/1992 | Bosley et al. | |
| 5,234,447 A | 8/1993 | Kaster et al. | |
| 5,297,536 A | 3/1994 | Wilk | |
| 5,346,501 A | 9/1994 | Regula et al. | |
| 5,391,156 A | 2/1995 | Hildwein et al. | |
| 5,429,131 A | 7/1995 | Scheinman et al. | |

(Continued)

FOREIGN PATENT DOCUMENTS

| | | |
|---|---|---|
| DE | 197 04 211 | 8/1998 |
| EP | 1077047 A2 | 2/2001 |

(Continued)

OTHER PUBLICATIONS

International Search Report and Written Opinion of International Search Authority for PCT/US2010/053514 dated Dec. 6, 2010.

(Continued)

*Primary Examiner* — Corrine M McDermott
*Assistant Examiner* — Robert Lynch
(74) *Attorney, Agent, or Firm* — Brinks Hofer Gilson & Lione

(57) ABSTRACT

The present embodiments provide medical apparatuses and methods for rapidly forming an anastomosis between two viscera. The medical apparatus generally comprises affixing a clamp to an elongate member. The method generally comprises positioning and then deploying the medical apparatus between and within two stomas via an elongate member.

20 Claims, 9 Drawing Sheets

(56) References Cited

U.S. PATENT DOCUMENTS

| | | |
|---|---|---|
| 5,458,131 A | 10/1995 | Wilk |
| 5,554,183 A | 9/1996 | Nazari |
| 5,562,683 A | 10/1996 | Chan |
| 5,562,688 A | 10/1996 | Riza |
| 5,571,090 A | 11/1996 | Sherts |
| 5,571,119 A | 11/1996 | Atala |
| 5,573,540 A | 11/1996 | Yoon |
| 5,573,543 A | 11/1996 | Akopov et al. |
| 5,578,044 A | 11/1996 | Gordon et al. |
| 5,582,615 A | 12/1996 | Foshee et al. |
| 5,584,835 A | 12/1996 | Greenfield |
| 5,586,986 A | 12/1996 | Hinchliffe |
| 5,593,414 A | 1/1997 | Shipp et al. |
| 5,630,824 A | 5/1997 | Hart |
| 5,643,292 A | 7/1997 | Hart |
| 5,643,317 A | 7/1997 | Pavcnik et al. |
| 5,645,552 A | 7/1997 | Sherts |
| 5,653,717 A | 8/1997 | Ko et al. |
| 5,665,067 A | 9/1997 | Linder et al. |
| 5,667,527 A | 9/1997 | Cook et al. |
| 5,674,231 A | 10/1997 | Green et al. |
| 5,683,402 A | 11/1997 | Cosgrove et al. |
| 5,690,656 A | 11/1997 | Cope et al. |
| 5,693,060 A | 12/1997 | Martin |
| 5,695,525 A | 12/1997 | Mulhauser et al. |
| 5,700,273 A | 12/1997 | Buelna et al. |
| 5,728,113 A | 3/1998 | Sherts |
| 5,728,116 A | 3/1998 | Rosenman |
| 5,741,278 A | 4/1998 | Stevens |
| 5,746,751 A | 5/1998 | Sherts |
| 5,779,720 A | 7/1998 | Walder-Utz et al. |
| 5,788,625 A | 8/1998 | Plouhar et al. |
| 5,792,153 A | 8/1998 | Swain et al. |
| 5,810,848 A | 9/1998 | Hayhurst |
| 5,824,010 A | 10/1998 | McDonald |
| 5,836,955 A | 11/1998 | Buelna et al. |
| 5,836,956 A | 11/1998 | Buelna et al. |
| 5,846,253 A | 12/1998 | Buelna et al. |
| 5,860,990 A | 1/1999 | Nobis et al. |
| 5,865,791 A | 2/1999 | Whayne et al. |
| 5,865,836 A | 2/1999 | Miller |
| 5,868,763 A | 2/1999 | Spence et al. |
| 5,873,530 A | 2/1999 | Chizinsky |
| 5,891,159 A | 4/1999 | Sherman et al. |
| 5,902,228 A | 5/1999 | Schulsinger et al. |
| 5,908,428 A | 6/1999 | Scirica et al. |
| 5,919,184 A | 7/1999 | Tilton, Jr. |
| 5,931,844 A | 8/1999 | Thompson et al. |
| 5,938,668 A | 8/1999 | Scirica et al. |
| 5,947,997 A | 9/1999 | Pavcnik et al. |
| 5,948,000 A | 9/1999 | Larsen et al. |
| 5,951,531 A | 9/1999 | Ferdman et al. |
| 5,968,078 A | 10/1999 | Grotz |
| 5,972,002 A | 10/1999 | Bark et al. |
| 5,976,159 A | 11/1999 | Bolduc et al. |
| 5,984,949 A | 11/1999 | Levin |
| 6,007,515 A | 12/1999 | Epstein et al. |
| 6,015,414 A | 1/2000 | Werp et al. |
| 6,021,776 A | 2/2000 | Allred et al. |
| 6,030,365 A | 2/2000 | Laufer |
| 6,059,749 A | 5/2000 | Marx |
| 6,077,217 A | 6/2000 | Love et al. |
| 6,086,608 A | 7/2000 | Ek et al. |
| 6,110,183 A | 8/2000 | Cope |
| 6,113,612 A | 9/2000 | Swanson et al. |
| 6,149,658 A | 11/2000 | Gardiner et al. |
| 6,152,935 A | 11/2000 | Kammerer et al. |
| 6,152,937 A | 11/2000 | Peterson et al. |
| 6,156,006 A | 12/2000 | Brosens et al. |
| 6,159,223 A | 12/2000 | Danks et al. |
| 6,171,321 B1 | 1/2001 | Gifford, III et al. |
| 6,183,486 B1 | 2/2001 | Snow et al. |
| 6,193,732 B1 | 2/2001 | Frantzen et al. |
| 6,200,329 B1 | 3/2001 | Fung et al. |
| 6,290,674 B1 | 9/2001 | Roue et al. |
| 6,293,952 B1 | 9/2001 | Brosens et al. |
| 6,293,961 B2 | 9/2001 | Schwartz et al. |
| 6,319,271 B1 | 11/2001 | Schwartz et al. |
| 6,328,727 B1 | 12/2001 | Frazier et al. |
| 6,348,059 B1 | 2/2002 | Hathaway et al. |
| 6,355,050 B1 | 3/2002 | Andreas et al. |
| 6,368,300 B1 | 4/2002 | Fallon et al. |
| 6,402,765 B1 | 6/2002 | Monassevitch et al. |
| 6,419,669 B1 | 7/2002 | Frazier et al. |
| 6,423,087 B1 | 7/2002 | Sawada |
| 6,428,550 B1 | 8/2002 | Vargas et al. |
| 6,494,889 B1 | 12/2002 | Fleischman et al. |
| 6,527,753 B2 | 3/2003 | Sekine et al. |
| 6,535,764 B2 | 3/2003 | Imran et al. |
| 6,569,173 B1 | 5/2003 | Blatter et al. |
| 6,572,629 B2 | 6/2003 | Kalloo et al. |
| 6,689,062 B1 | 2/2004 | Mesallum |
| 6,918,871 B2 | 7/2005 | Schulze |
| 7,128,708 B2 | 10/2006 | Saadat et al. |
| 7,232,448 B2 | 6/2007 | Battles et al. |
| 7,273,451 B2 | 9/2007 | Sekine et al. |
| 7,351,202 B2 | 4/2008 | Long |
| 7,431,694 B2 | 10/2008 | Stefanchik et al. |
| 7,585,308 B2 | 9/2009 | Weisenburgh, II et al. |
| 7,591,828 B2 | 9/2009 | Ortiz |
| 7,608,086 B2 | 10/2009 | Tanaka et al. |
| 7,618,427 B2 | 11/2009 | Ortiz et al. |
| 7,637,919 B2 | 12/2009 | Ishikawa et al. |
| 7,654,951 B2 | 2/2010 | Ishikawa |
| 7,666,197 B2 | 2/2010 | Orban, III |
| 7,691,103 B2 | 4/2010 | Fernandez et al. |
| 7,708,748 B2 | 5/2010 | Weisenburgh, II et al. |
| 7,713,278 B2 | 5/2010 | Hess et al. |
| 7,725,214 B2 | 5/2010 | Diolaiti |
| 2001/0049497 A1 | 12/2001 | Kalloo et al. |
| 2002/0022851 A1 | 2/2002 | Kalloo et al. |
| 2003/0216613 A1 | 11/2003 | Suzuki et al. |
| 2003/0225312 A1 | 12/2003 | Suzuki et al. |
| 2004/0087985 A1 | 5/2004 | Loshakove et al. |
| 2004/0092975 A1 | 5/2004 | Loshakove et al. |
| 2004/0097801 A1 | 5/2004 | Mesallum |
| 2004/0225191 A1 | 11/2004 | Sekine et al. |
| 2004/0249367 A1 | 12/2004 | Saadat et al. |
| 2005/0004584 A1 | 1/2005 | Franco et al. |
| 2005/0101837 A1 | 5/2005 | Kalloo et al. |
| 2005/0107664 A1 | 5/2005 | Kalloo et al. |
| 2005/0277965 A1 | 12/2005 | Brenneman et al. |
| 2005/0277981 A1 | 12/2005 | Maahs et al. |
| 2006/0025654 A1 | 2/2006 | Suzuki et al. |
| 2006/0025788 A1 | 2/2006 | Loshakove et al. |
| 2006/0036267 A1 | 2/2006 | Saadat et al. |
| 2006/0100480 A1 | 5/2006 | Ewers et al. |
| 2006/0167482 A1 | 7/2006 | Swain et al. |
| 2006/0178560 A1 | 8/2006 | Saadat et al. |
| 2006/0200004 A1 | 9/2006 | Wilk |
| 2006/0211919 A1 | 9/2006 | Wilk |
| 2006/0212063 A1 | 9/2006 | Wilk |
| 2006/0229653 A1 | 10/2006 | Wilk |
| 2006/0237022 A1 | 10/2006 | Chen et al. |
| 2006/0237023 A1 | 10/2006 | Cox et al. |
| 2006/0241344 A1 | 10/2006 | Wilk |
| 2006/0241480 A1 | 10/2006 | Wilk |
| 2006/0241570 A1 | 10/2006 | Wilk |
| 2006/0241651 A1 | 10/2006 | Wilk |
| 2006/0241691 A1 | 10/2006 | Wilk |
| 2006/0252997 A1 | 11/2006 | Wilk |
| 2006/0253123 A1 | 11/2006 | Wilk |
| 2006/0258909 A1 | 11/2006 | Saadat et al. |
| 2006/0264986 A1 | 11/2006 | Park et al. .................. 606/153 |
| 2006/0287666 A1 | 12/2006 | Saadat et al. |
| 2006/0293701 A1 | 12/2006 | Ainsworth et al. ......... 606/153 |
| 2007/0004958 A1 | 1/2007 | Ohdaira |
| 2007/0051380 A1 | 3/2007 | Pasricha |
| 2007/0100375 A1 | 5/2007 | Mikkaichi et al. |
| 2007/0100376 A1 | 5/2007 | Mikkaichi et al. |
| 2007/0106313 A1 | 5/2007 | Golden et al. |
| 2007/0112362 A1 | 5/2007 | Mikkaichi et al. |
| 2007/0123840 A1 | 5/2007 | Cox |
| 2007/0163585 A1 | 7/2007 | Uesugi et al. |

| | | |
|---|---|---|
| 2007/0163596 A1 | 7/2007 | Mikkaichi et al. |
| 2007/0163604 A1 | 7/2007 | Mikkaichi et al. |
| 2007/0167675 A1 | 7/2007 | Miyamoto et al. |
| 2007/0167676 A1 | 7/2007 | Miyamoto et al. |
| 2007/0167967 A1 | 7/2007 | Mikkaichi et al. |
| 2007/0173859 A1 | 7/2007 | Mikkaichi et al. |
| 2007/0173867 A1 | 7/2007 | Brenneman ............ 606/153 |
| 2007/0197864 A1 | 8/2007 | Dejima et al. |
| 2007/0198000 A1 | 8/2007 | Miyamoto et al. |
| 2007/0198033 A1 | 8/2007 | Kalloo et al. |
| 2007/0208360 A1 | 9/2007 | Demarais et al. |
| 2007/0213702 A1 | 9/2007 | Kogasaka et al. |
| 2007/0213749 A1 | 9/2007 | Kogasaka et al. |
| 2007/0213750 A1 | 9/2007 | Weadock |
| 2007/0219411 A1 | 9/2007 | Dejima et al. |
| 2007/0225642 A1* | 9/2007 | Houser et al. ............ 604/93.01 |
| 2007/0225734 A1 | 9/2007 | Bell et al. |
| 2007/0255100 A1 | 11/2007 | Barlow et al. |
| 2007/0255165 A1 | 11/2007 | Uesugi et al. |
| 2007/0255273 A1 | 11/2007 | Fernandez et al. |
| 2007/0260214 A1 | 11/2007 | Mikkaichi et al. |
| 2007/0270629 A1 | 11/2007 | Charles |
| 2008/0015408 A1 | 1/2008 | Paolitto et al. |
| 2008/0021277 A1 | 1/2008 | Stefanchik |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065105 A1 | 3/2008 | Larkin et al. |
| 2008/0065106 A1 | 3/2008 | Larkin |
| 2008/0065107 A1 | 3/2008 | Larkin et al. |
| 2008/0065108 A1 | 3/2008 | Diolaiti |
| 2008/0065109 A1 | 3/2008 | Larkin |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0097489 A1 | 4/2008 | Goldfarb et al. |
| 2008/0114378 A1 | 5/2008 | Matsushita |
| 2008/0119868 A1 | 5/2008 | Sharp et al. |
| 2008/0125804 A1 | 5/2008 | Gostout |
| 2008/0154290 A1 | 6/2008 | Golden et al. |
| 2008/0161641 A1 | 7/2008 | Nakazato et al. |
| 2008/0171907 A1 | 7/2008 | Long et al. |
| 2008/0183039 A1 | 7/2008 | Long et al. |
| 2008/0200762 A1 | 8/2008 | Stokes et al. |
| 2008/0208161 A1 | 8/2008 | Kaji et al. |
| 2008/0228029 A1 | 9/2008 | Mikkaichi et al. |
| 2008/0228203 A1 | 9/2008 | Bell et al. |
| 2008/0249416 A1 | 10/2008 | Sato |
| 2008/0275297 A1 | 11/2008 | Bakos et al. |
| 2008/0287963 A1 | 11/2008 | Rogers et al. |
| 2008/0312502 A1 | 12/2008 | Swain et al. |
| 2009/0023985 A1 | 1/2009 | Ewers |
| 2009/0054728 A1 | 2/2009 | Trusty |
| 2009/0054761 A1 | 2/2009 | Voegele et al. |
| 2009/0182195 A1 | 7/2009 | Faller et al. |
| 2009/0221915 A1 | 9/2009 | Voegele et al. |
| 2009/0227828 A1 | 9/2009 | Swain et al. |
| 2009/0276055 A1 | 11/2009 | Harris et al. |
| 2009/0281559 A1 | 11/2009 | Swain et al. |
| 2010/0010520 A1 | 1/2010 | Takahashi et al. |
| 2010/0036399 A1 | 2/2010 | Viola |
| 2010/0056861 A1 | 3/2010 | Spivey |
| 2010/0063521 A1 | 3/2010 | Manzo |
| 2010/0087842 A1 | 4/2010 | Heinrich et al. |
| 2010/0094319 A1 | 4/2010 | Heinrich et al. |
| 2010/0099947 A1 | 4/2010 | Sato et al. |
| 2010/0113872 A1 | 5/2010 | Asada et al. |
| 2010/0114124 A1 | 5/2010 | Kelleher et al. |
| 2010/0160729 A1 | 6/2010 | Smith et al. |
| 2010/0179510 A1 | 7/2010 | Fox et al. |
| 2010/0179540 A1 | 7/2010 | Marczyk et al. |
| 2010/0198232 A1 | 8/2010 | Diolaiti |

FOREIGN PATENT DOCUMENTS

| | | |
|---|---|---|
| EP | 1493391 A1 | 1/2005 |
| GB | 877903 | 9/1961 |
| WO | WO 98/02316 | 1/1998 |
| WO | WO/2006-121855 | 11/2006 |
| WO | WO 2009/006444 | 1/2009 |

OTHER PUBLICATIONS

Specification Sheet—FUJINON Maximizing Productivity for Double Balloon Endoscopy System (3 pages).

Hagen, et al., Hybrid natural orifice transluminal endoscopic surgery (NOTES) for Roux-en-Y gastric bypass: an experimental surgical study in human cadavers, 2008, pp. 918-924, vol. 40.

Fritscher-Ravens, EUS—Experimental and Evolving Techniques, 2006, pp. S95-S99, vol. 38.

Fritscher-Ravens, et al., Comparative study of NOTES alone vs. EUS-guided NOTES procedures, 2008, pp. 925-930, vol. 40.

Bories, et al., Transgastric endoscopic ultrasonography- guided biliary drainage: results of a pilot study, 2007, pp. 287-291, vol. 39.

Will, et al., Treatment of biliary obstruction in selected patients by endoscopic ultrasonography (EUS)-guided transluminal biliary drainage, 2007, pp. 292-295, vol. 39.

* cited by examiner

PLANAR CLAMPS FOR ANASTOMOSIS

CROSS-REFERENCE TO RELATED APPLICATIONS

This application claims the benefit of U.S. Provisional Patent Application No. 61/257,654 filed on Nov. 3, 2009, entitled "PLANAR CLAMPS FOR ANASTOMOSIS," the entire contents of which are incorporated herein by reference.

FIELD OF THE INVENTION

The present embodiments relate generally to medical apparatuses for forming an anastomosis between two viscera, and more particularly relates to forming a side-to-side anastomosis such as a gastrojejunostomy.

BACKGROUND OF THE INVENTION

Historically, gastrointestinal (GI) surgery has been performed to create a channel between two viscera for the purpose of redirecting bodily fluids, i.e., an anastomosis. It will be recognized that there may be a need to anastomose many different viscera, such as the jejunum and the stomach (gastrojejunostomy), the bile duct and the duodenum, two sections of the small or large intestines, or various other combinations of viscera such as during bariatric surgery.

During surgery to form an anastomosis, the two tissues are often brought together and affixed to one another using fixators such as sutures, staples, or some other fixation means. While fixators are being placed, the tissues of the respective viscera are held in proximity to one another using various means. In open surgery, this is usually accomplished with graspers, forceps, or other tissue holding instruments manipulated by clinicians. In laparoscopic surgery, similar instruments may be used, except the laparotic access limits the number of instruments to a few percutaneous "ports," making the technical challenge of the procedure much greater.

When these types of GI surgery are performed, there exists the potential to breach the mural boundary. Thus, extreme care must be taken to prevent contamination of the pleural and abdominal cavities with GI contents, which are laden with bacteria that do not naturally occur in those locations. If significant contamination occurs, then serious infection can set-in, which can lead to serious illness or death if not treated early and vigorously.

To address some of these limitations and to minimize the invasiveness of such surgeries, magnetic anastomosis devices (MADs) were developed for forming anastomosis. For example, a MAD may consist of two magnet cores surrounded by metal rims. The two magnet cores are positioned in the two viscera between which the anastomosis is desired. Due to the magnetic attraction between the cores, the walls of the two adjacent viscera are compressed. The compression of the walls of the viscera results in ischemic necrosis to produce an anastomosis between the two viscera. When using MADs, it is sometimes necessary to conduct a second procedure to insert a stent or other device to maintain the anastomosis that the MADs created. A second procedure requires additional costs, patient and physician time, and involves certain risks associated with any endoscopic procedure. Also when using MADs, the distal magnet must be placed in the intestine, usually the jejunum, which requires the use of an intestinal lumen. For patients with tumors or strictures, it may be difficult for an endoscope and/or the distal magnet to pass through. In addition, when using MADs an anastomosis is created over a several day period, rather than being created immediately at the time of the procedure.

SUMMARY OF THE PREFERRED EMBODIMENTS

The present embodiments provide medical apparatuses and a method for rapidly forming an anastomosis between two viscera while reducing the technical challenge and minimizing the potential risk of prior techniques for forming anastomoses. The anastomosis may be formed with surety before the patient leaves the medical facility and eliminates the need for a follow-up procedure. Additional protection against breach of the mural boundary is provided and there is minimal risk of the anastomosis becoming separated or forming a leak while the patient is not in the medical facility.

According to one embodiment, a medical apparatus for approximating the tissues of two viscera includes affixing to the end of an elongate member a medical device that includes two clamps, each clamp including an exterior clamp member and an interior clamp member, and then inserting the medical device through the bodily walls of two viscera. The interior clamp members define an interior space between them sized to permit formation of the anastomosis therebetween and to maintain the anastomosis, while the movable exterior and interior clamp members compress the two viscera and maintain them in close proximity. The medical device is held to the end of the elongate member and delivered via a tubular cap; alternatively, the elongate member itself holds the medical device and delivers it. Further, the medical device may be held on a separate elongate member, such as a catheter, that runs alongside the elongate member.

According to more detailed aspects of the medical device, the movable clamps each have an exterior clamp member and an interior clamp member that move between a delivery state and a deployed state, wherein the clamp members are biased toward the deployed state. In the deployed state, the exterior and interior clamp members are coplanar. In the delivery state, the exterior clamp members and the interior clamp members move away from each other, out of plane, so that the exterior clamp members are more proximate to each other and the two interior clamp members are more proximate to each other.

A method for forming an anastomosis between two viscera is also provided in accordance with the teachings of the present embodiments. Generally, two stomas are created in two viscera, the stomas are brought into proximity with each other, and then the medical device with the two clamps as described above is provided and inserted into the stomas. The medical device is positioned such that the exterior clamp members and the interior clamp members compress the walls of the two viscera between them and hold the walls proximate to each other.

According to more detailed aspects of the method, the size of the anastomosis may be immediately enlarged by using a knife or other cutting device to excise additional tissue from the walls of the two viscera located within the interior space defined by the interior clamp members. The excising step may be performed endoscopically, and the cutting instrument may be introduced through a working channel of an endoscope.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally away from the medical professional and/or towards a target site within a patient's anatomy during a medical procedure.

Figure 1:
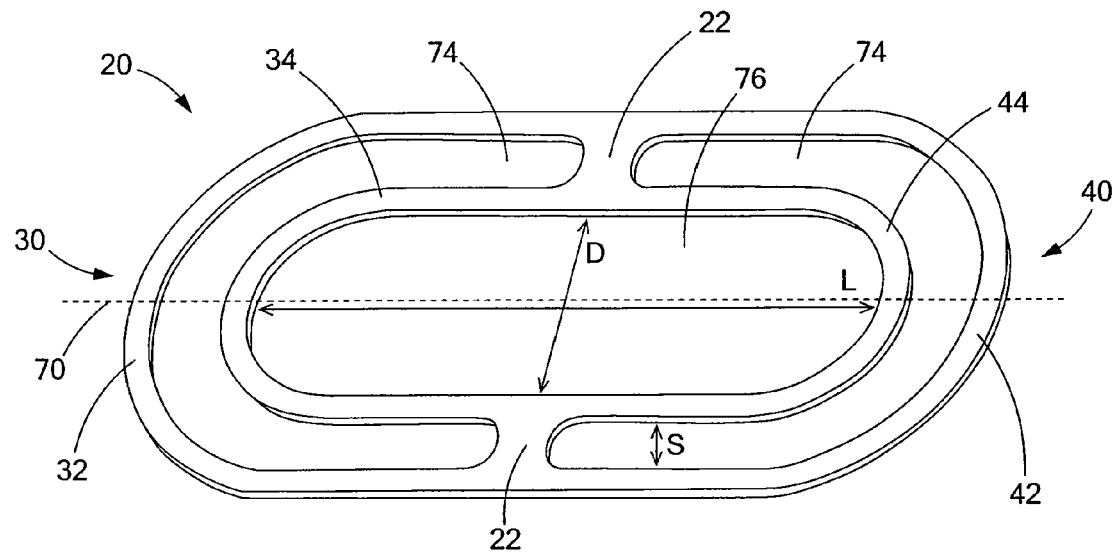
FIG. 1 is a perspective view of a preferred embodiment of a medical device in a deployed state for forming an anastomosis.
Figure 2:
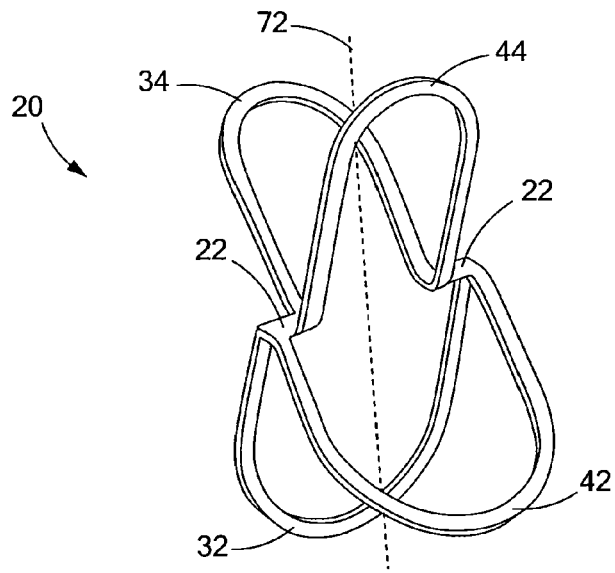
FIG. 2 is a perspective view of the medical device depicted in FIG. 1 in a delivery state.

Referring now to FIGS. 1 to 2, an embodiment of a medical device 20 is depicted for forming an anastomosis, such as during an endoscopic procedure. As will be discussed herein, the medical device 20 serves to clamp the tissue surrounding an anastomosis, hold it open, as well as facilitate enlargement of the anastomosis. The medical device 20 generally includes a first clamp 30 and a second clamp 40 defining a lateral axis 70 and a longitudinal axis 72, positioned opposite each other along the lateral axis 70, i.e., opposite each other relative to the longitudinal axis 72. The first clamp 30 has a first exterior clamp member 32 and a first interior clamp member 34. The first exterior and interior clamp members 32 and 34 connect to each other via intermediate portions 22. The second clamp 40 has a second exterior clamp member 42 and a second interior clamp member 44, and the second exterior clamp member 42 connects to the second interior clamp member 44 via the intermediate portions 22.

As depicted, the exterior and interior clamp members have a general U-shape, although they could be V-shaped, semi-rectangular in shape, or any other semi-annular shape. As depicted, the interior clamp members are located concentrically within the exterior clamp members along the lateral axis 70.

As depicted in FIG. 1, the medical device 20 is in a deployed state wherein the exterior clamp members 32 and 42 and the interior clamp members 34 and 44 of the first clamp 30 and the second clamp 40 are coplanar. Coplanar as used herein means perfectly planar and +/−30 degrees away from perfectly planar.

FIG. 2 depicts the medical device 20 in the delivery state wherein the exterior and interior clamp members 32, 42, 34, and 44 have rotated out of plane toward the longitudinal axis 72 so that the first exterior clamp member 32 is adjacent to the second exterior clamp member 42 and the first interior clamp member 34 is adjacent to the second interior clamp member 44. The clamp members typically will rotate about 60° to about 110° degrees away from the lateral axis 70.

In the embodiment shown in FIGS. 1 and 2, the clamp members are biased toward forming the deployed state as depicted in FIG. 1. The medical device 20 is shown as being formed of a flat metal—preferably nitinol—having a round or rectangular (flat) cross-sectional shape, although other constructions may be employed (e.g., a round wire). Preferably, the metal has a thickness in the range of about 0.001 to about 0.1 inches, and more preferably from about 0.008 to about 0.028 inches. For example, the medical device 20, or the clamp members individually, may be comprised of other metals, metal alloys, plastics, or other materials that have suitable resiliency, whereby the clamp members can move according to the natural or imposed shape-memory characteristics of the clamp members. The medical device 20, or the clamp members individually, may also be comprised of resorbable or degradable materials, but preferably the material would not substantially degrade or lose structural integrity until formation of the anastomosis was complete. As used herein, resorbable refers to the ability of a material to be absorbed into a tissue and/or bodily fluid upon contact with the tissue and/or bodily fluid. A number of resorbable materials are known in the art, and any suitable resorbable material may be used. Examples include resorbable homopolymers, copolymers, or blends of resorbable polymers. As used herein, degradable refers to the ability of a material to dissipate upon implantation within a body within a clinically reasonable amount of time, independent of the mechanisms by which dissipation can occur, such as dissolution, degradation, absorption and excretion. A number of degradable materials are known in the art, and any suitable degradable material may be used. Examples include polyethylene, polypropylene and polyoxypropylene glycolic sugars, as well as polylactic sugars.

In addition, the medical device 20 is shown as comprising one solid piece of metal. In alternative embodiments, the intermediate portions 22 may be fastening devices known in the art, such as hinges, springs, or other rotatable couplings known in the art. In these embodiments, the clamp members need not have shape-memory characteristics. Moreover, while the first and second clamps 30 and 40 make up one unitary device as depicted in FIGS. 1 and 2, the medical device 20 may comprise two separate clamp members (not shown), or it may comprise four separate clamp members (not shown).

Referring again to FIG. 1, an interior space 74 exists between the exterior clamp members and the interior clamp members. The distance S between the exterior clamp members and the interior clamp members may range from about 0 to about 8 mm. A second interior space 76 exists between the first and second interior clamp members 34 and 44. The horizontal distance D between the two intermediate portions 22 may range from about 0 to about 25 mm, and the lateral distance L from the first interior clamp member 34 to the second interior clamp member 44 may range from about 5 mm to about 50 mm.

A medical apparatus 66 for forming an anastomosis will now be described with reference to FIGS. 3A to 5. The medical apparatus 66 includes a medical device for forming, creating, and maintaining an anastomosis, an elongate member for delivering the medical device, and, optionally, a tubular cap for retaining the medical device on or near the elongate member. According to one embodiment shown in FIG. 3A, the medical device 20 is shown loaded within a tubular cap 64 and adjacent to a distal end 62 of an elongate member, in this case an endoscope 60. The endoscope 60 may be any type of scope known in the art, or may alternatively be any flexible elongate member suitable for being inserted into the body for therapeutic purposes. The medical device 20 is held in the delivery configuration by the tubular cap 64. In this embodiment, a control wire 61 is passed through an accessory channel 65 and is connected to a pusher 63. The control wire 61 in combination with the pusher 63 is used to move the exterior clamp members 32 and 42 distally beyond the distal end 67 of the tubular cap 64 so that the exterior clamp members 32 and 42 may be released into their deployed states. The control wire 61 and pusher 63 are then further extended to deploy the interior clamp members 34 and 44. Alternatively, the medical device 20 could be loaded into the endoscope 60 itself, and the endoscope 60 would maintain the medical device 20 in the delivery configuration.

Figure 4:
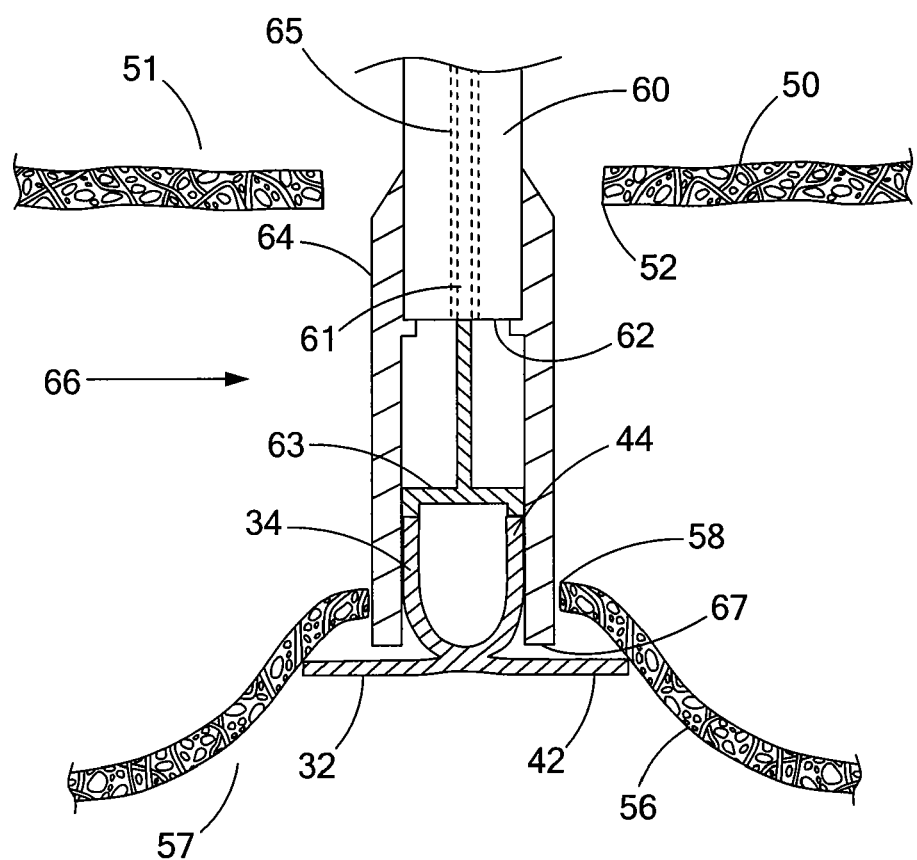
FIG. 4 is a front view, partially in cross-section, of the apparatus of FIG. 3A, with the medical device of FIG. 1 partially deployed.

Referring now to FIG. 4, the medical device 20 has been inserted distally through a first stoma 52 in a first bodily wall 50 (e.g., the stomach) and through a second stoma 58 in a second bodily wall 56 (e.g., the small intestine, and typically, the jejunum) to rest within the interior 57 of the second bodily wall 56. In this embodiment of the apparatus, the control wire 61 and pusher 63 have been advanced by the clinician in the distal direction, thereby moving the exterior clamp members 32 and 42 beyond the distal end 67 of the tubular cap 64 and allowing the exterior clamp members 32 and 42 to move to their deployed states. Releasing the exterior clamp members 32 and 42 into their deployed states causes the exterior clamp members 32 and 42 to exert pressure on the interior surface of the second bodily wall 56.

Figure 5:
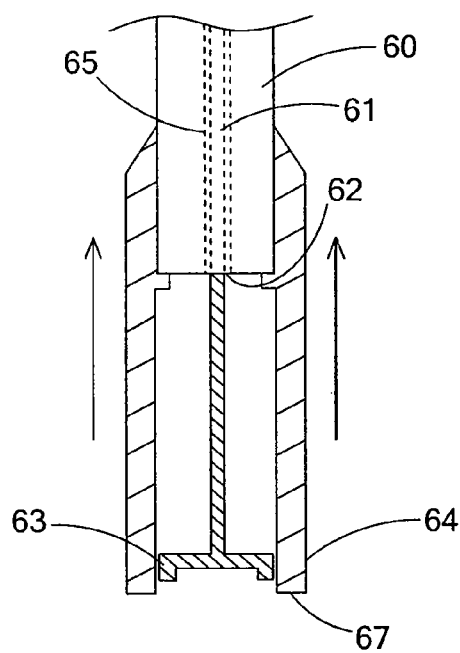
FIG. 5 is a front view, partially in cross-section, of the apparatus of FIG. 3A, with the medical device of FIG. 1 fully deployed.
Figure 5:
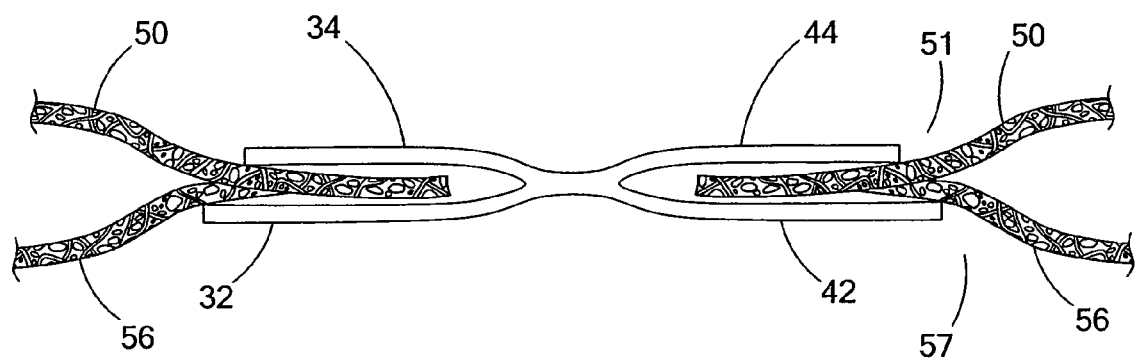

Referring now to FIG. 5, the apparatus 66 has been retracted so that the second bodily wall 56 is brought proximate to the first bodily wall 50, and the interior clamp members 34 and 44 are located proximal to the first bodily wall 50. The control wire 61 and pusher 63 are further extended, thereby releasing the interior clamp members 34 and 44 into their deployed states, causing the interior clamp members 34 and 44 to exert pressure on the interior surface of the first bodily wall 50. Alternatively, or in conjunction with the control wire 61, the whole apparatus 66 can be pulled proximally and the tension of the exterior clamp members 32, 42 on the second bodily wall 56 can pull the interior clamp members 34, 44 out of the tubular cap 64 by overcoming the friction therebetween. The medical device 20 could also be loaded such that interior clamp members 34 and 44 are located distal to the exterior clamp members 32 and 42 such that the interior clamp members 34 and 44 are deployed within the interior 57 of the second bodily wall 56, and the exterior clamp members 32 and 42 are deployed within an interior 51 of the first bodily wall 50 (not shown).

Figure 3A:
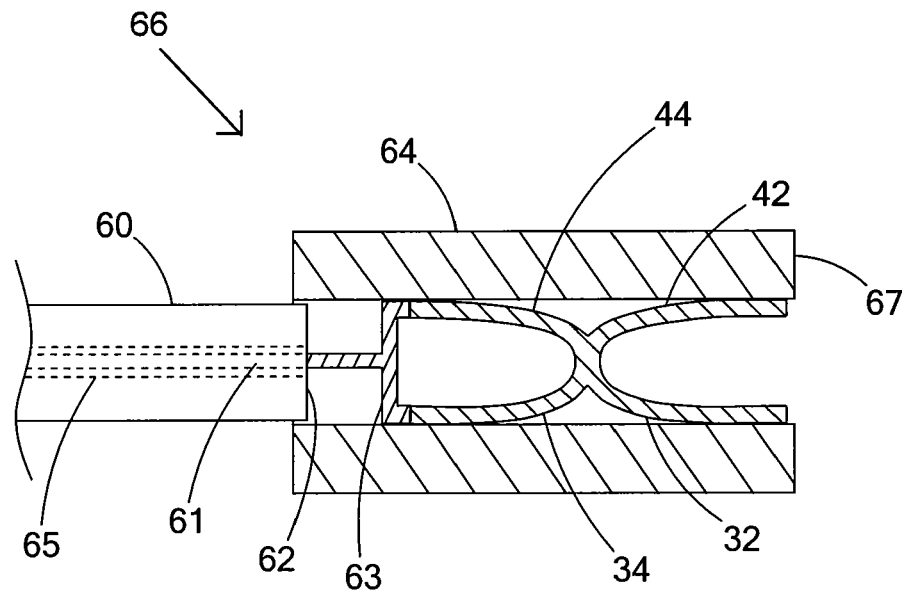
FIG. 3A is a side view, partially in cross-section, of an apparatus for forming an anastomosis which includes the medical device of FIG. 1 in the delivery state and a control wire to deploy the medical device.
Figure 3B:
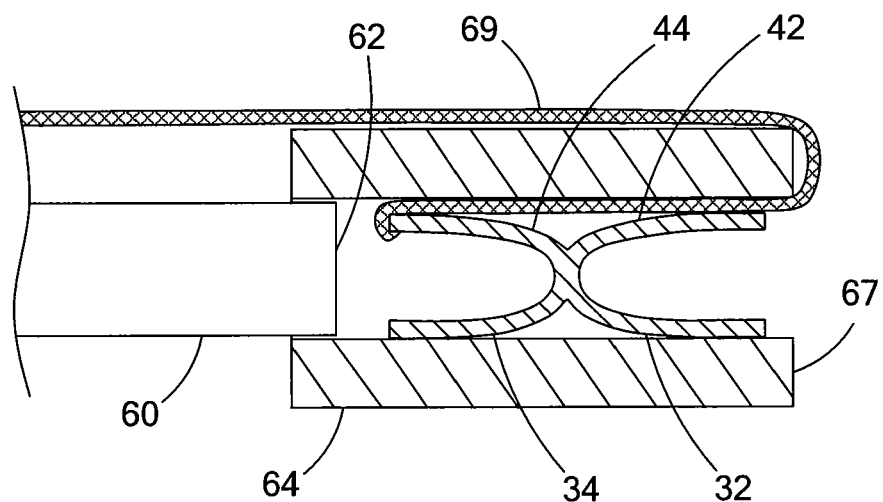
FIG. 3B is a side view, partially in cross-section, of an apparatus for forming an anastomosis which includes the medical device of FIG. 1 in the delivery state and a tether to deploy the medical device.

There are alternative ways to facilitate the deployment of the medical device 20 within the two stomas 52 and 58. One embodiment is depicted in FIG. 3B. In this embodiment, a tether is used to move the medical device 20 distally out from the tubular cap 64. The tether may be a suture or strap or other material known in the art, and may be affixed to the medical device 20 via knots, catches, enlargements, by tying it, or through other means known in the art, or may merely be located adjacent to and engaged by friction between the medical device 20 and the tubular cap 64. In the embodiment depicted in FIG. 3B, the tether is a suture 69 tied to the medical device 20. When the clinician pulls the suture 69 proximally, the medical device 20 is moved distally so that exterior clamp members 32 and 42 are no longer constrained by the tubular cap 64, thereby allowing them to move to their deployed states. Pulling further proximally on the suture 69 causes the interior clamp members 34 and 44 to move to their deployed states once they are no longer constrained by the tubular cap 64. The suture may then be excised by the clinician via a cutting device advanced through a working lumen (not shown) in the endoscope 60.

Figure 6:
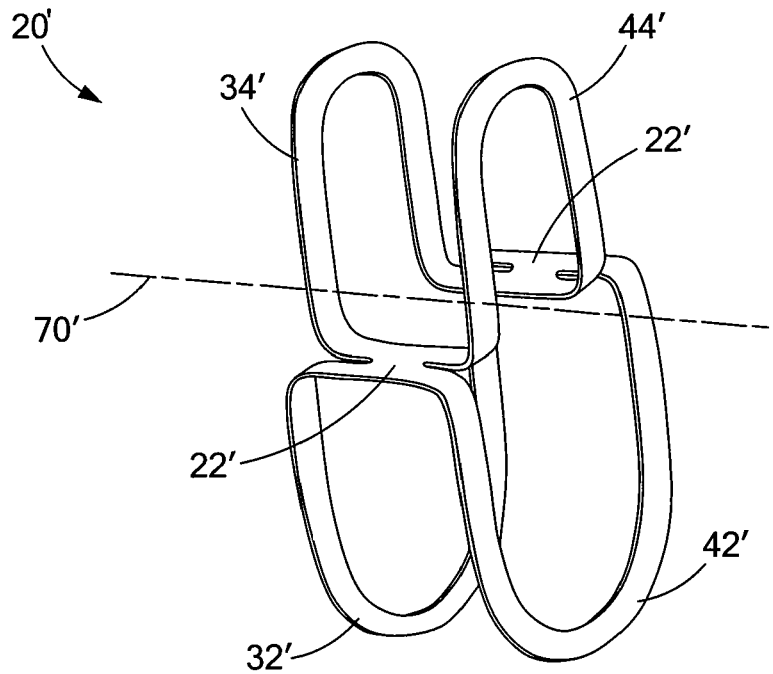
FIG. 6 is a perspective view of another embodiment of a medical device in a delivery state for forming an anastomosis.

Referring now to FIGS. 6-9, alternative embodiments of the medical device and the tubular cap are shown. FIG. 6 depicts an alternative embodiment of the medical device 20'. In medical device 20', the exterior and interior clamp members 32', 42', 34', and 44' rotate at locations further away laterally from the intermediate portion 22' than the exterior and interior clamp members 32, 42, 34, and 44 do from intermediate portion 22 in medical device 20. This difference in rotation allows the medical device 20' to better fit within the retractable cap 73 depicted in FIG. 7 and the tubular cap 83 depicted in FIG. 9.

Figure 7:
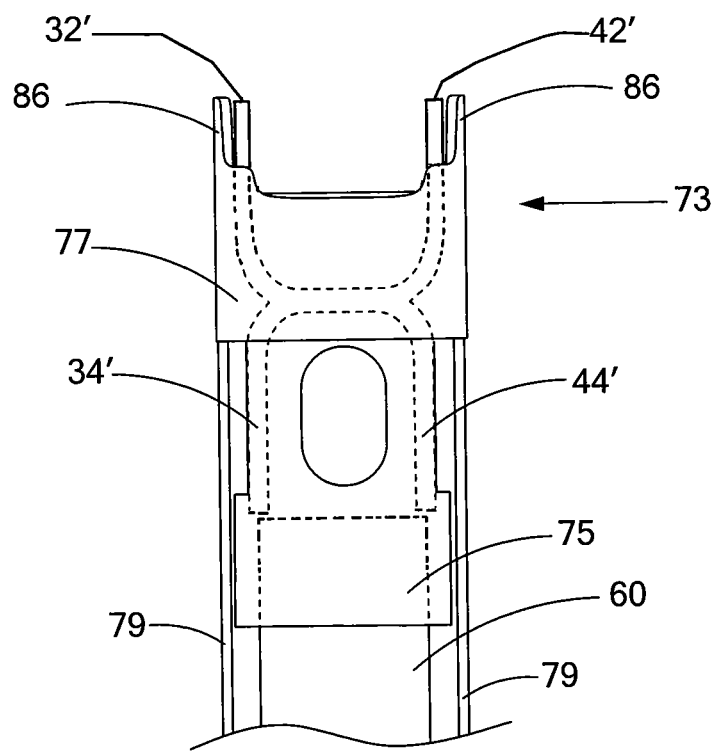
FIG. 7 is a front view of an apparatus for forming an anastomosis which includes the medical device of FIG. 6 contained within one embodiment of a tubular cap.
Figure 8:
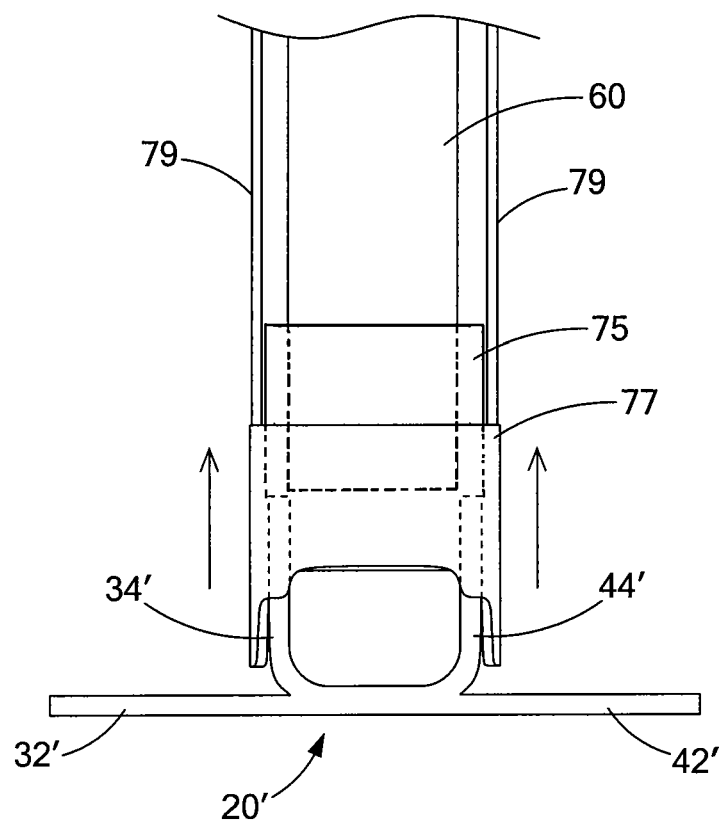
FIG. 8 is a front view of the apparatus of FIG. 7 with the medical device partially deployed.

FIG. 7 depicts an embodiment of the tubular cap 64 wherein the tubular cap 64 is a retractable cap 73. The retractable cap 73 is comprised of a fixed end portion 75 and a retractable hood 77 that is slidably mounted on the exterior of the fixed end portion 75. The retractable hood 77 contains two control wings 86 opposite each other that maintain the exterior clamp members 32' and 42' in their delivery configurations. The retractable cap 73 may be placed on an endoscope 60, or it may be placed on a separate elongate member, such as a catheter, that runs alongside the endoscope 60 either freely or on a wire guide (not shown). Two external drive wires 79 are attached to the retractable hood 77. Referring now to FIGS. 7-8, a clinician may pull proximally on the drive wires 79, which will move the retractable hood 77 proximally, and will release and deploy the exterior clamp members 32 and 42. The interior clamp members 34 and 44 may be released and deployed either by pushing the medical device 20 in the distal direction, for example by using a control wire 61 and pusher 63 as discussed above, or by pulling the endoscope 60 away in the proximate direction.

Figure 9:
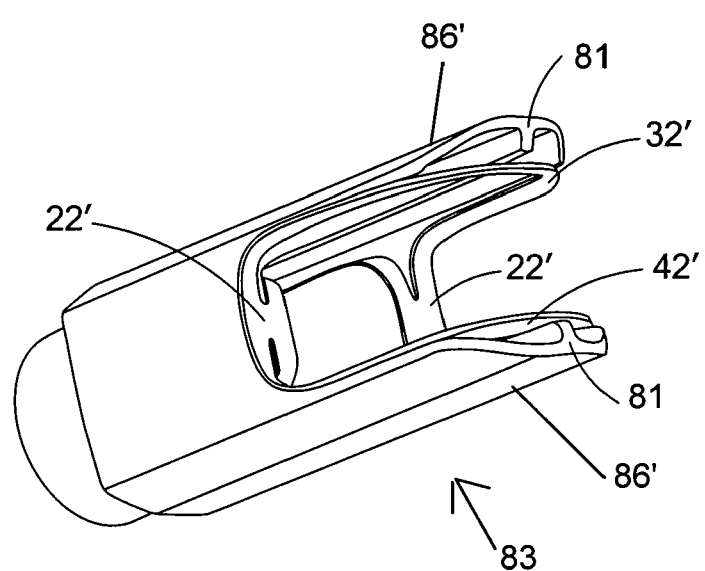
FIG. 9 is a perspective view of another embodiment of a tubular cap with the medical device of FIG. 6 contained within the tubular cap.

Referring now to FIG. 9, another embodiment of the tubular cap 64 is shown. FIG. 9 depicts a tubular cap 83 with grooves 81 contained on the interior of two control wings 86'. The control wings 86' maintain the exterior clamp members 32' and 42' in the delivery configuration. The grooves 81 better allow a tether to be used in conjunction with the tubular cap 83 by holding the tether in place. Alternatively, a perfectly cylindrical cap may be used as depicted in FIGS. 3A-5. Other shapes and designs may be used and will be known to those of skill in the art.

A medical method for creating an anastomosis will now be described with reference to FIGS. 3A-5, and 11-12. Before fully deploying the medical device 20 to create an anastomosis, stomas must be created in the desired viscera, and the stomas must be brought within proximity of each other. One way to achieve this goal would be to load the medical device 20 within a tubular cap 64 at the distal end 62 of an endoscope 60 as depicted in FIGS. 3A-5, and then advance the endoscope to the first viscera. A cutting device (not shown) could be advanced through a working lumen of the endoscope 60 and could be used to create the first stoma 52 in the first bodily wall 50 of the first viscera. The endoscope 60 could be further advanced to the second viscera, and the cutting device could be used to create the second stoma 58 in the second bodily wall 56. The exterior clamp members 32 and 42 could be deployed as described above, and then the medical device 20, endoscope 60 and tubular cap 64, and the second bodily wall 56 could be retracted toward the first stoma 52 in the first bodily wall 50. Once the medical device 20 is properly positioned such that the interior clamp members 34 and 44 are located proximal to the first bodily wall 50, the interior clamp members 34 and 44 could be released as described above and the anastomosis would be created.

The stomas may also be created and brought into proximity with one another prior to insertion of the medical device 20. There are numerous ways of achieving this that are known in the art, some of which are described in U.S. Nonprovisional application Ser. No. 12/025,985, filed Feb. 5, 2008, which is incorporated by reference herein in its entirety. Laparoscopic surgery or open surgery and devices used in those types of surgeries may also be employed to create the stomas and to hold them in place proximal to each other to prepare for the insertion of the medical device 20.

Figure 12:
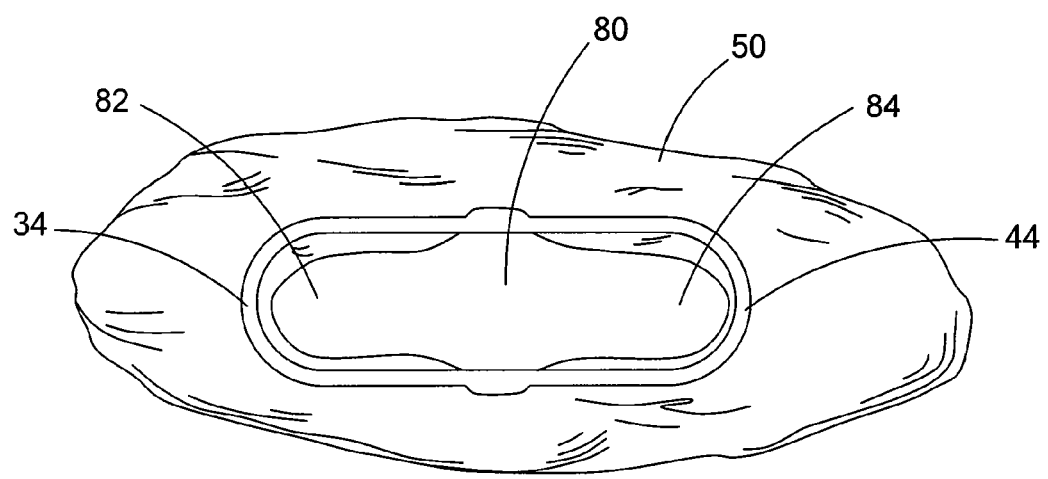
FIG. 12 is a top view of the embodiment of FIG. 1 deployed in tissue where additional incisions have been made to enlarge the anastomosis.

Once the stomas have been created and the medical device 20 has been deployed via the elongate member as described above and depicted in FIGS. 3A-5, the force exerted by the interior clamp members 34 and 44 against the first bodily wall 50 and the force exerted by the exterior clamp members 32 and 42 against the second bodily wall 56 compress the two bodily walls and hold them proximate to each other. The compression exerted on the bodily walls by the exterior and interior clamp members will result in necrosis of the tissues of the two viscera that are contained between the clamp members, thus resulting in an even larger anastomosis after a few days or a week, depending on the thickness of the tissues and the strength of the material used for the clamp members. If a larger anastomosis is immediately desired, a knife or other cutting device may be used to excise the tissue from the two bodily walls by cutting from the interior 80 laterally toward the apex of the first interior clamp member 34 to create a larger opening 82 as depicted in FIG. 12. Additionally, an incision may be extended laterally from the interior 80 to the apex of the second interior clamp member 44 to form a second larger opening 84, so that one large, continuous anastomosis is now formed.

Figure 10:
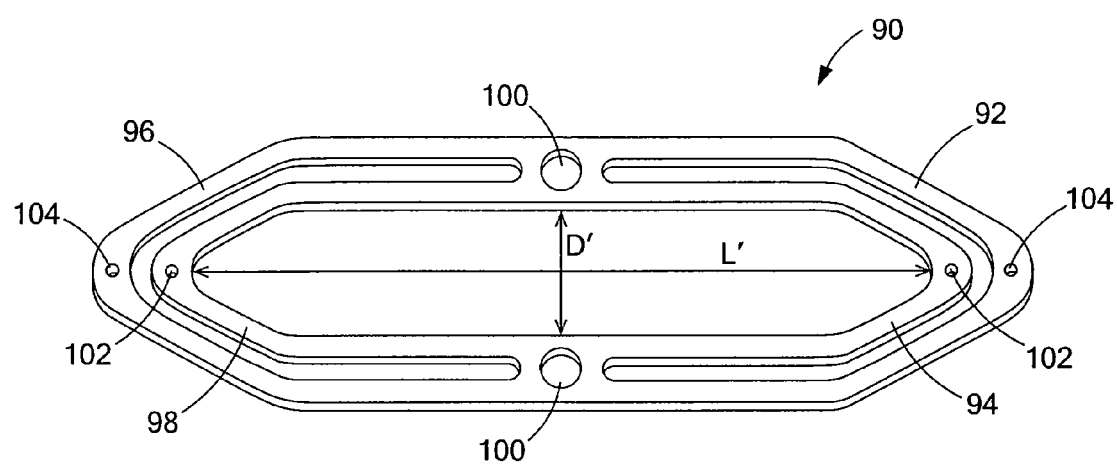
FIG. 10 is a perspective view of another embodiment of a medical device in a deployed state for forming an anastomosis.
Figure 11:
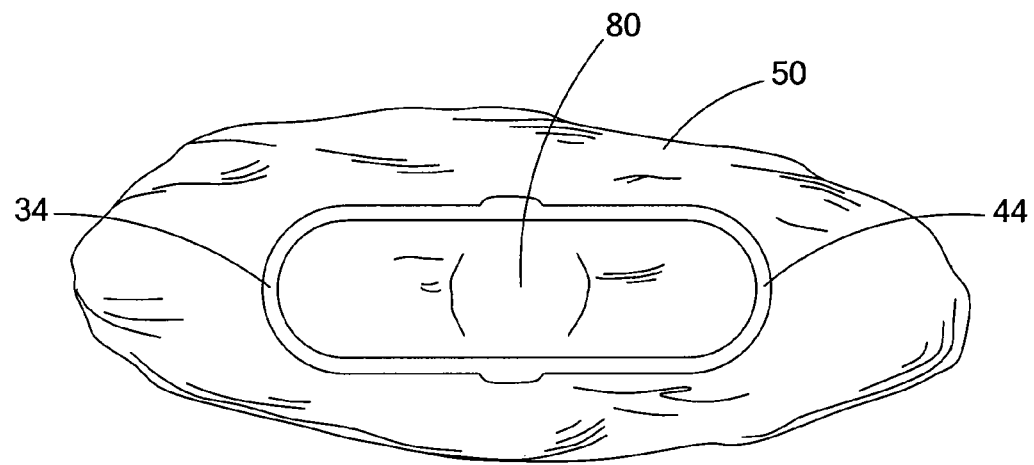
FIG. 11 is a top view of the embodiment of FIG. 1 deployed in tissue.
Figure 13:
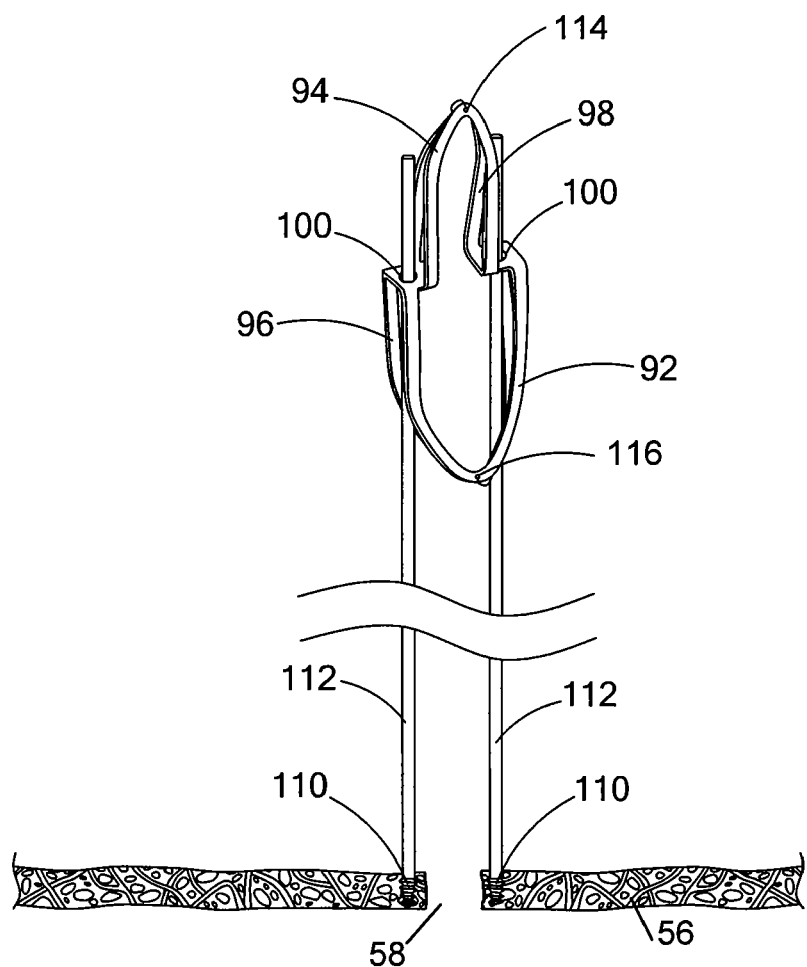
FIG. 13 is a front view of an apparatus for forming an anastomosis which includes the medical device of FIG. 10 in the delivery state.

An alternate method for creating an anastomosis will now be described with reference to FIGS. 4-5, 10 and 13. In this method, a gastronomy would be created as described above, and then two screw retractors 110 attached to torque cables 112 would be advanced through the first stoma 52 of the first bodily wall 50 and anchored to the proximal side of the second bodily wall 56 on either side of the second stoma 58 as depicted in FIG. 13. The clinician would then remove the endoscope 60, leaving the anchored screw retractors 110 and torque cables 112 extending proximally and exiting the patient's mouth. The medical device 90, which as depicted in FIG. 10 is substantially identical to medical device 20 except that it has been modified to include two large holes 100 to fit over the torque cables 112, would then be constrained in a delivery state similar to the delivery states of medical device 20 depicted in FIG. 2 and medical device 20' depicted in FIG. 6. The length L' between first interior clamp member 98 and second interior clamp member 94 ranges from about 5 mm to about 50 mm, and the horizontal distance D' ranges from about 0 mm to about 25 mm.

As depicted in FIG. 13, a suture 114 is advanced through holes 102 to keep the interior clamp members 98 and 94 adjacent to each other in the delivery state, and another suture 116 would be advanced through holes 104 in first exterior clamp member 96 and second exterior clamp member 92 to hold them adjacent to each other in the delivery state and located distally to the interior clamp members 98 and 94. It would be known by those of skill in the art that rings, bands, or other materials may be used in place of the sutures 114 and 116. The medical device 90 in the delivery state is loaded on to the torque cables 112 by inserting the proximal end of the torque cables 112 through the large holes 100 in the medical device 90.

Referring still to FIG. 13, the medical device 90 would then be advanced over the torque cables 112 through the first stoma 52 until the exterior clamp members 96 and 92 have advanced through the second stoma 58. The clinician may optionally pull proximally on the torque cables 112 in order to pull the tissue of the second bodily wall 56 proximate to the exterior clamp members 96 and 92. The clinician will then release the exterior clamp members 96 and 92 by pulling on or excising the suture 116, thereby causing the exterior clamp members 96 and 92 to deploy and exert pressure on the interior surface of the second bodily wall 56. The clinician will then pull proximally on the torque cables 112 until the second stoma 58 is adjacent to the first stoma 52 and the interior clamp members 98 and 94 are proximate to the first stoma 52. The clinician will then release the interior clamp members 98 and 94 to their deployed states in the same manner in which the exterior clamp members 96 and 92 were released, causing the interior clamp members 98 and 94 to exert pressure on the interior surface of the first bodily wall 50. The clinician then removes the screw retractors 110 and the torque cables 112 by pulling them proximally away from the newly formed gastronomy.

Removal of the medical device 20, medical device 20', or medical device 90 may be completed through natural means. The pressure exerted on the bodily walls 50 and 56 will cause necrosis over a number of days, thereby forming an anastomosis that is slightly larger than interior 80 or interior 80 and openings 82 and 84 combined. After a certain amount of necrosis occurs, the medical devices 20, 20', and 90 will dislodge and pass through the body naturally. Or, the medical devices 20, 20', and 90 may be made of degradable or resorbable materials so that it will be naturally broken down by the body.

It will be recognized by those skilled in the art that during these anastomosis formation procedures, the area of compression of the bodily walls 50 and 56 provides a barrier that guards against leakage of the GI contents or other bodily fluids depending on the viscera involved. Likewise, the anastomosis is formed with surety before the patient leaves the medical facility, eliminating the need for a follow-up procedure. Moreover, because interior clamp members 34 and 44 maintain the size of the anastomosis, there is no need for a second procedure to insert a stent to maintain the opening.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An apparatus for facilitating the creation of an anastomosis in bodily tissue, the apparatus comprising:
   a first clamp comprising a first exterior clamp member and a first interior clamp member, the first clamp operable between a deployed configuration and a delivery configuration, the first clamp being biased towards the deployed configuration;
   a second clamp comprising a second exterior clamp member and a second interior clamp member, the second clamp operable between a deployed configuration and a delivery configuration, the second clamp being biased towards the deployed configuration;
   the interior and exterior clamp members of the first clamp connected together at their ends by hinged regions, and the interior and exterior clamp members of the second clamp connected together at their ends by the hinged regions;
   the exterior and interior clamp members of the first clamp being coplanar in the deployed configuration, and the exterior and interior clamp members of the second clamp being coplanar in the deployed configuration; and
   the exterior and interior clamp members of the first clamp being moved away from each other, out of plane, in the delivery configuration, and the exterior and interior clamp members of the second clamp being moved away from each other, out of plane, in the delivery configuration.

2. The apparatus of claim 1 wherein the first clamp and second clamp are unitarily formed as a single piece.

3. The apparatus of claim 1 wherein the first clamp and second clamp are diametrically opposed.

4. The apparatus of claim 1 wherein the first and second clamps are formed of a resilient material that flexes to permit the first and second clamps to move between their deployed and delivery configurations.

5. The apparatus of claim 1 wherein the hinged regions each include apertures sized to receive elongate delivery cables.

6. The apparatus of claim 1 wherein the first and second exterior clamp members each include a small hole such sized to receive a first suture, the first suture tying the first and second exterior clamp members together to maintain the delivery state thereof, and wherein the first and second interior clamp members each include a small hole such sized to receive a second suture, the second suture tying the first and second interior clamp members together to maintain the delivery state thereof.

7. The apparatus of claim 1 wherein the interior and exterior members of both the first clamp and second clamp together define an annular shape.

8. The apparatus of claim 7 wherein a gap exists between the exterior and interior members, the gap spanning a distance less than a thickness of a tissue into which the apparatus is deployed.

9. The apparatus of claim 7 wherein the first interior member defines a first interior space, and wherein the second interior member defines a second interior space, and wherein the first and second interior spaces are in communication with each other.

10. The apparatus of claim 7, wherein the first and second clamps define a lateral axis, and wherein the interior and exterior clamp members of the first clamp are concentrically arranged about a first point on the lateral axis, wherein the interior and exterior clamp members of the second clamp are concentrically arranged about a second point on the lateral axis.

11. An apparatus for facilitating the creation of an anastomosis in bodily tissue, the apparatus comprising:
    a first clamp comprising a first exterior clamp member and a first interior clamp member, the first clamp operable between a deployed configuration and a delivery configuration, the first clamp being biased towards the deployed configuration;
    a second clamp comprising a second exterior clamp member and a second interior clamp member, the second clamp operable between a deployed configuration and a delivery configuration, the second clamp being biased towards the deployed configuration;
    the exterior and interior clamp members of the first clamp being coplanar in the deployed configuration, and the exterior and interior clamp members of the second clamp being coplanar in the deployed configuration;
    the exterior and interior clamp members of the first clamp being moved away from each other, out of plane, in the delivery configuration, and the exterior and interior clamp members of the second clamp being moved away from each other, out of plane, in the delivery configuration; and
    an elongate tubular member defining a longitudinal axis, wherein the first and second clamps are sized to fit within the elongate tubular member in their delivery configuration and maintain their bias towards the deployed configuration, and upon release from the tubular member automatically move towards the deployed configuration.

12. The apparatus of claim 11 wherein the tubular member further includes a tubular cap fit on an exterior of a distal end of the tubular member for maintaining the first and second clamps in the delivery configuration.

13. The apparatus of claim 12 wherein the tubular cap is slidably attached to the tubular member and may be proximally retracted relative to the distal end to release the first and second clamps.

14. An apparatus for facilitating the creation of an anastomosis in bodily tissue, the apparatus comprising:
    an exterior annular member being elongated in a lateral direction, the exterior annular member forming an enclosed elongated ring and defining a first interior space;
    an interior annular member being elongated in the lateral direction, the interior annular member being received within the first interior space, the interior annular member forming an enclosed elongated ring and defining a second interior space; and
    hinged regions connecting the exterior and interior annular members, the hinged regions structured to permit the exterior and interior annular members to move relative to each other.

15. The apparatus of claim 14, wherein the second interior space is elongated in the lateral direction.

16. The apparatus of claim 14, wherein the exterior and interior annular members are concentrically arranged about a common longitudinal axis.

17. The apparatus of claim 14, wherein the exterior and interior annular members are arranged to be coplanar in a lateral plane.

18. The apparatus of claim 17, wherein the exterior and interior annular members are formed of a resilient material that flexes to permit the exterior and interior annular members to move out of the lateral plane.

19. The apparatus of claim 14, wherein the hinged regions are structured such that opposite lateral ends of the exterior annular member may move towards each other in a first longitudinal direction while opposite lateral ends of the interior annular member may move towards each other in a second longitudinal direction opposite the first longitudinal direction.

20. The apparatus of claim 19, wherein the exterior and interior annular members are biased towards each other, and further comprising an elongate tubular member defining a longitudinal axis, and further comprising a delivery configuration wherein opposite lateral ends of the interior annular member are moved towards each other and fit within the elongate tubular member to maintain their bias towards the exterior annular member, and opposite lateral ends of the exterior annular member are moved towards each other and fit within the elongate tubular member to maintain their bias towards the interior annular member, and upon release from the tubular member the opposite lateral ends of the exterior and interior annular member automatically move towards each other.

\* \* \* \* \*